(12) United States Patent
Manke et al.

(10) Patent No.: US 9,078,974 B2
(45) Date of Patent: Jul. 14, 2015

(54) SYRINGE HAVING DUAL PIVOTING ARM PLUNGER ROD

(71) Applicant: Becton Dickinson France, S.A.S., Le Pont-de-Claix (FR)

(72) Inventors: Darrin Scott Manke, North Andover, MA (US); Christopher Labak, Brookline, MA (US); Joseph Omer St. Cyr, Salem, NH (US)

(73) Assignee: Becton Dickinson France, S.A.S., Le Pont-de-Claix (FR)

( * ) Notice: Subject to any disclaimer, the term of this patent is extended or adjusted under 35 U.S.C. 154(b) by 303 days.

(21) Appl. No.: 13/622,381

(22) Filed: Sep. 19, 2012

(65) Prior Publication Data
US 2013/0085458 A1 Apr. 4, 2013

Related U.S. Application Data

(60) Provisional application No. 61/541,589, filed on Sep. 30, 2011.

(51) Int. Cl.
*A61M 5/315* (2006.01)
*A61M 5/24* (2006.01)
A61M 5/34 (2006.01)
A61M 5/31 (2006.01)

(52) U.S. Cl.
CPC ............. *A61M 5/31511* (2013.01); *A61M 5/24* (2013.01); *A61M 5/31515* (2013.01); *A61M 5/344* (2013.01); *A61M 5/347* (2013.01); *A61M 2005/3104* (2013.01); *A61M 2005/31518* (2013.01)

(58) Field of Classification Search
CPC ...................... A61M 5/31511; A61M 5/31515; A61M 2005/31518
USPC .................. 604/110, 187, 218, 223, 227, 233, 604/191–198, 228
See application file for complete search history.

(56) References Cited

U.S. PATENT DOCUMENTS

| 4,011,868 A | 3/1977 | Friend |
| 4,581,023 A | 4/1986 | Kuntz |
| 5,902,278 A * | 5/1999 | Aguilar .......................... 604/227 |
| 8,556,495 B2 * | 10/2013 | Axen et al. ..................... 366/189 |

(Continued)

FOREIGN PATENT DOCUMENTS

| DE | 188449 C | 10/1906 | |
| DE | 19923131 A1 * | 11/2000 | ............ A61M 5/315 |

(Continued)

*Primary Examiner* — Nicholas Lucchesi
*Assistant Examiner* — Justin L Zamory
(74) *Attorney, Agent, or Firm* — The Webb Law Firm

(57) ABSTRACT

A syringe assembly includes a syringe barrel having a first end, a second end, and a sidewall extending between the first end and the second end. The syringe assembly further includes a stopper disposed within a chamber of the syringe barrel, a plunger adapter engaged with the stopper and defining a recessed portion therein, and first and second plunger arms each having a first end pivotally secured to the plunger adapter. The first and second plunger arms each have a pre-use position where the plunger arms are spaced from each other, and a use position where the plunger arms are positioned adjacent to each other and configured to displace the stopper relative to the syringe barrel. The recessed portion of the plunger adapter receives a portion of a first end of a plunger rod when the first and second plunger arms are in the pre-use position and the use position.

24 Claims, 16 Drawing Sheets

(56) References Cited

U.S. PATENT DOCUMENTS

| | | |
|---|---|---|
| 2011/0046560 A1 | 2/2011 | Schiller et al. |
| 2011/0046569 A1 | 2/2011 | Lum et al. |
| 2011/0046603 A1 | 2/2011 | Felsovalyi et al. |

FOREIGN PATENT DOCUMENTS

| | | |
|---|---|---|
| WO | 2010034462 A1 | 4/2010 |
| WO | 2012056265 A1 | 5/2012 |

* cited by examiner

SYRINGE HAVING DUAL PIVOTING ARM PLUNGER ROD

CROSS-REFERENCE TO RELATED APPLICATION

This application claims priority to U.S. Provisional Patent Application Ser. No. 61/541,589 filed Sep. 30, 2011, the entire disclosure of which is hereby incorporated by reference.

BACKGROUND OF THE INVENTION

1. Field of the Invention

The present invention relates to a syringe adapted for delivery of a fluid and/or collection of a fluid, and, more particularly, to a syringe having a dual pivoting arm plunger rod.

2. Description of Related Art

Syringe assemblies, and in particular hypodermic syringes, are well known in the medical field for dispensing fluids, such as medication. A conventional syringe typically includes a syringe barrel with an opening at one end and a plunger mechanism disposed through the other end. The plunger typically includes a plunger rod extending through the barrel, with a plunger head or stopper at the end of the plunger rod within the barrel and with a finger flange at the other end of the plunger rod extending out of the barrel. In use, the plunger rod is retracted through the syringe barrel to fill the syringe barrel with a fluid, such as a medication, with the plunger rod extending out from the rear end of the syringe barrel. For delivery of the medication to a patient, the opening of the syringe barrel is adapted for fluid communication with a patient, such as through a hypodermic needle fitted at the front end of the syringe barrel or through a luer-type fitting extending from the front end of the syringe barrel for attachment with a fluid line of a patient. Upon depression of the plunger rod, the plunger rod and stopper travel through the syringe barrel, thereby forcing the contents of the syringe out through the opening at the front end for delivery to the patient. Such an operation is well known in the medical field, and medical practitioners have become well accustomed to the use of such common fluid delivery procedures through standard syringes.

Conventional syringes are well known to be used in connection with a vial of a medication, where the user draws the fluid into the syringe immediately prior to injection and delivery of the fluid to the patient. Oftentimes, hypodermic syringes may be packaged as "pre-filled" devices, wherein the syringe is pre-filled with medication prior to being packaged and delivered to the end user. In this manner, there is no need for the user to fill the device prior to injection, thereby saving time for the end user and maintaining consistent volumes for delivery.

Pre-filled syringes and pre-filled metered dose syringes are often filled with narcotics or other drugs at a production facility, packaged, and then shipped to a medical facility. Once at the facility, these syringes are often placed in controlled storage and/or locked cabinets to reduce theft of the syringes themselves and/or theft of the contents of these syringes. The space within these controlled storage locations is often limited, thus there is a need for a syringe assembly that has a smaller packaging footprint to reduce the storage space required for containing this syringe. It is also desirable to produce syringes that are uniform in terms of an outer surface shape to allow for stacking of the syringes within the storage cabinet.

SUMMARY OF THE INVENTION

In one embodiment, a syringe assembly includes a syringe barrel having a first end, a second end, and a sidewall extending between the first end and the second end. The syringe assembly further includes a stopper disposed within a chamber of the syringe barrel, a plunger adapter engaged with the stopper and defining a recessed portion therein, and first and second plunger arms each having a first end pivotally secured to the plunger adapter. The first and second plunger arms each have a pre-use position where the plunger arms are spaced from each other, and a use position where the plunger arms are positioned adjacent to each other and configured to displace the stopper relative to the syringe barrel. The recessed portion of the plunger adapter receives a portion of the first end of the plunger rod when the first and second plungers arms are in the pre-use position and the use position.

The stopper and the plunger adapter may be co-formed. The first and second plunger arms may each comprise an elongate body, with the first end of each plunger arm including one of a receiver and an engagement pivotally secured to the other of the receiver and the engagement positioned on the plunger adapter.

In a further embodiment, a syringe assembly includes a syringe barrel having a first end, a second end, and a sidewall extending between the first end and the second end, with the sidewall defining a chamber. The syringe assembly also includes a stopper disposed within the chamber of the syringe barrel, a plunger adapter engaged with the stopper, and first and second plunger arms each comprising an elongate body having a first end and a second end. The first end of each plunger arm includes one of a receiver and an engagement and the other of the receiver and the engagement engaged with the plunger adapter. The receiver is pivotally secured with the engagement. The first and second plunger arms each have a pre-use position where the first and second plunger arms are spaced from each other, and a use position where the first and second plunger arms are positioned adjacent to each other and configured to displace the stopper relative to the syringe barrel.

The stopper and the plunger adapter may be co-formed. The first and second plunger arms may be secured to each other when the first and second plunger arms are in the use position. The first and second plunger arms may be substantially parallel to a longitudinal axis of the syringe barrel when the first and second plunger arms are in the pre-use position. The first plunger arm may be positioned on an opposite side of the syringe barrel relative to the second plunger arm when the first and second plunger arms are in the pre-use position. The first plunger arm may have a locking protrusion and the second plunger arm may have a locking recess configured to receive and engage the locking protrusion of the first plunger arm. At least a portion of the elongate body of each plunger arm may be substantially L-shaped in cross-section. The plunger adapter may be formed separately from the stopper and comprise a stopper engaging portion secured to the stopper and a plunger interface portion secured to the first and second plunger arms. The plunger interface portion of the plunger adapter may be positioned outside of the chamber when the first and second plunger arms are in the pre-use position.

The first end of each plunger arm may include an extension extending from the elongate body of each plunger arm, and the receiver may be positioned on the extension of the first end of each plunger arm with the engagement positioned on the plunger adapter. Each receiver may comprise an opening corresponding to the extension of the first end of each plunger arm, and the engagement may comprise a pin-shaped member configured to be received by the respective receivers of the first and second plunger arms. The plunger adapter may include a first engagement configured to engage the receiver of the first plunger arm and a second engagement configured to engage the receiver of the second plunger arm. The syringe assembly may also include a medication or drug disposed within the syringe barrel.

In another embodiment, a syringe assembly includes a syringe barrel having a first end, a second end, and a sidewall extending between the first end and the second end, with the sidewall defining a chamber with a longitudinal axis extending therealong. The syringe assembly also includes a stopper disposed at least partially within the chamber, a plunger adapter engaged with the stopper and defining a recessed portion, and first and second plunger arms. Each plunger arm has a first end that is pivotally secured to the plunger adapter and transitionable from a pre-use position in which a portion of the first end of each plunger arm is secured to the plunger adapter and the first and second plunger arms extend adjacent to the syringe barrel, to a use position in which the first end of each plunger arm is entirely received within the recessed portion and the first and second plunger arms are positioned adjacent to each other.

The recessed portion may comprise a first L-shaped area configured to receive a portion of the first plunger arm and a second L-shaped area configured to receive a portion of the second plunger arm. The first L-shaped area may be offset from the second L-shaped area in a direction perpendicular to the longitudinal axis. The first and second plunger arms may each comprise an elongate body, with the first end of each plunger arm including a receiver pivotally secured to respective first and second engagements positioned on the plunger adapter. The first and second engagements of the plunger adapter may be offset for each other in a direction perpendicular to the longitudinal axis.

Further details and advantages of the invention will become clear upon reading the following detailed description in conjunction with the accompanying drawing figures, wherein like parts are designated with like reference numerals throughout.

DESCRIPTION OF PREFERRED EMBODIMENTS

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to FIGS. 1-11, a syringe assembly, generally indicated as 10, adapted for the dispensing and delivery of a fluid is shown. Syringe assembly 10 is intended for use for injection or infusion of fluid, such as a medication, directly into a patient, and is generally shown and described for purposes of the present description as a hypodermic syringe. Syringe assembly 10 is contemplated for use in connection with a needle such as by connecting syringe assembly 10 to a separate needle assembly (not shown), or alternatively for connection with a separate intravenous (IV) connection assembly (not shown).

Figure 1:
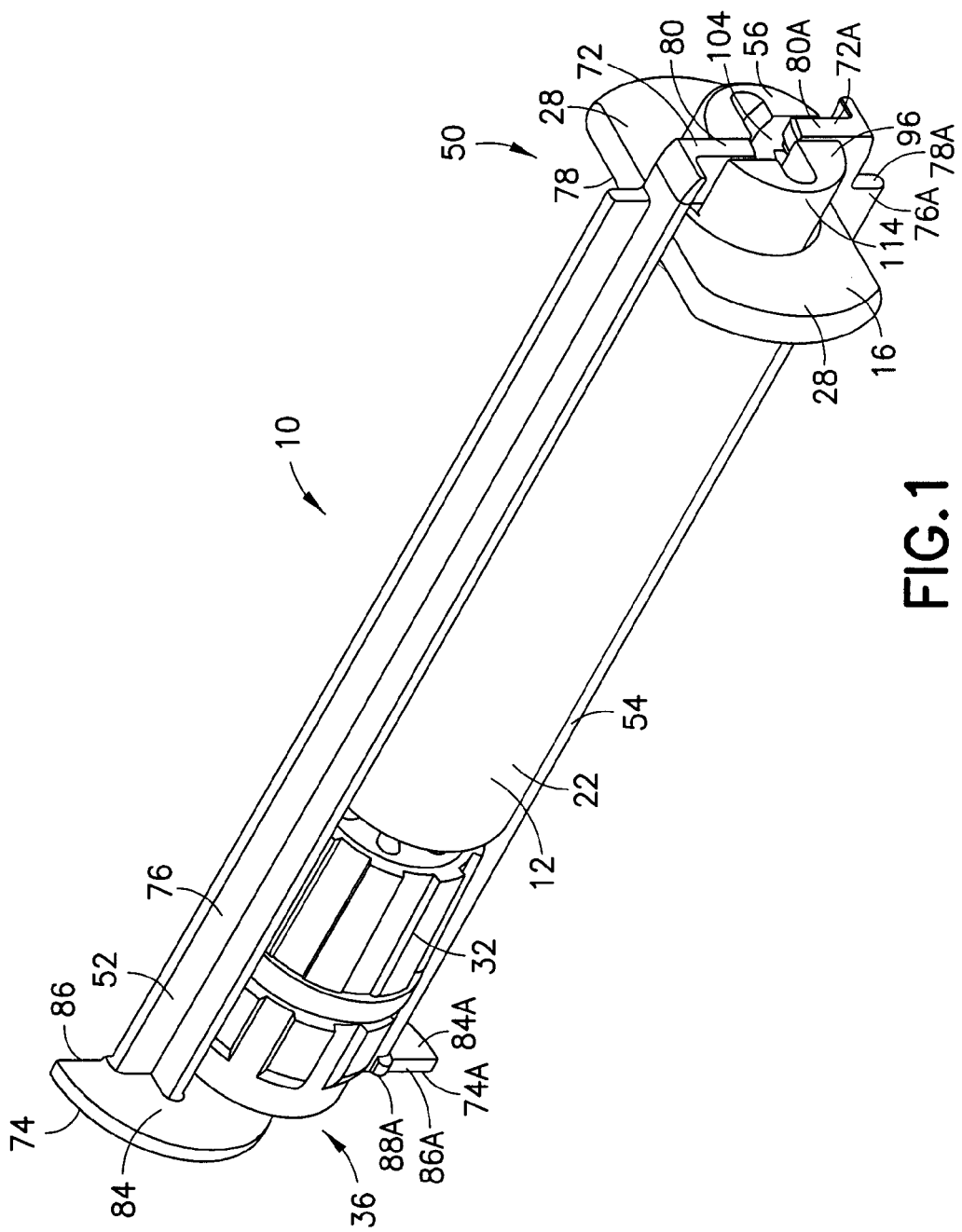
FIG. 1 is a perspective view of a syringe assembly in a pre-use position in accordance with an embodiment of the present invention.
Figure 2:
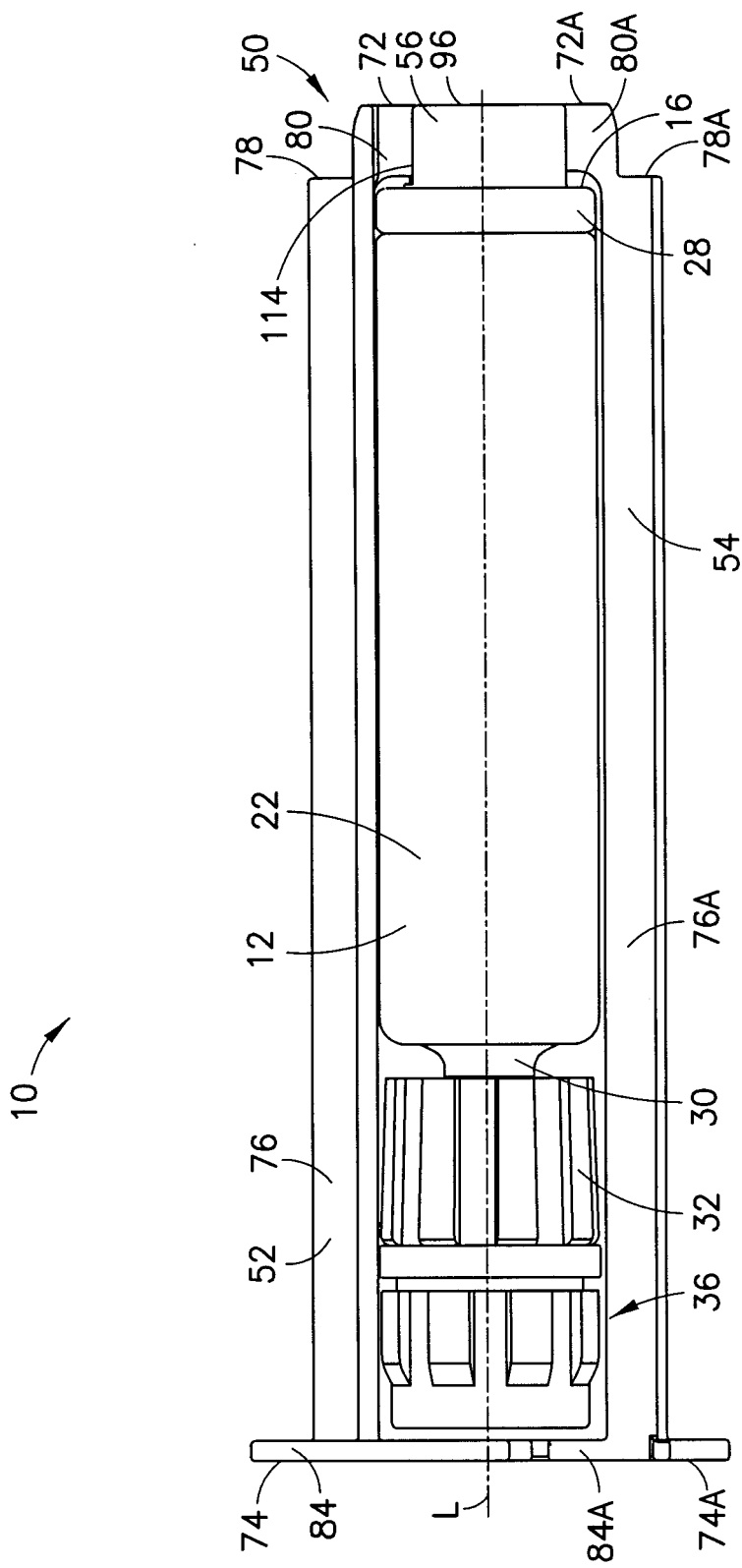
FIG. 2 is a front view of the syringe assembly of FIG. 1 in accordance with an embodiment of the present invention.
Figure 3:
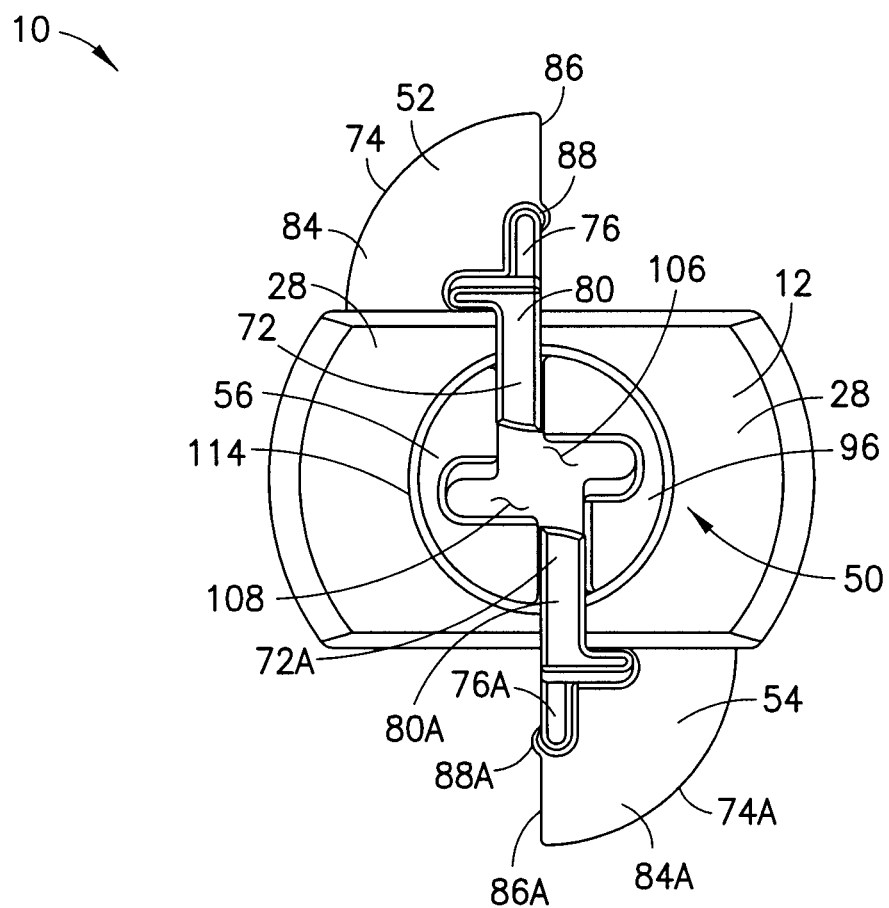
FIG. 3 is a right side view of the syringe assembly of FIG. 1 in accordance with an embodiment of the present invention.
Figure 4:
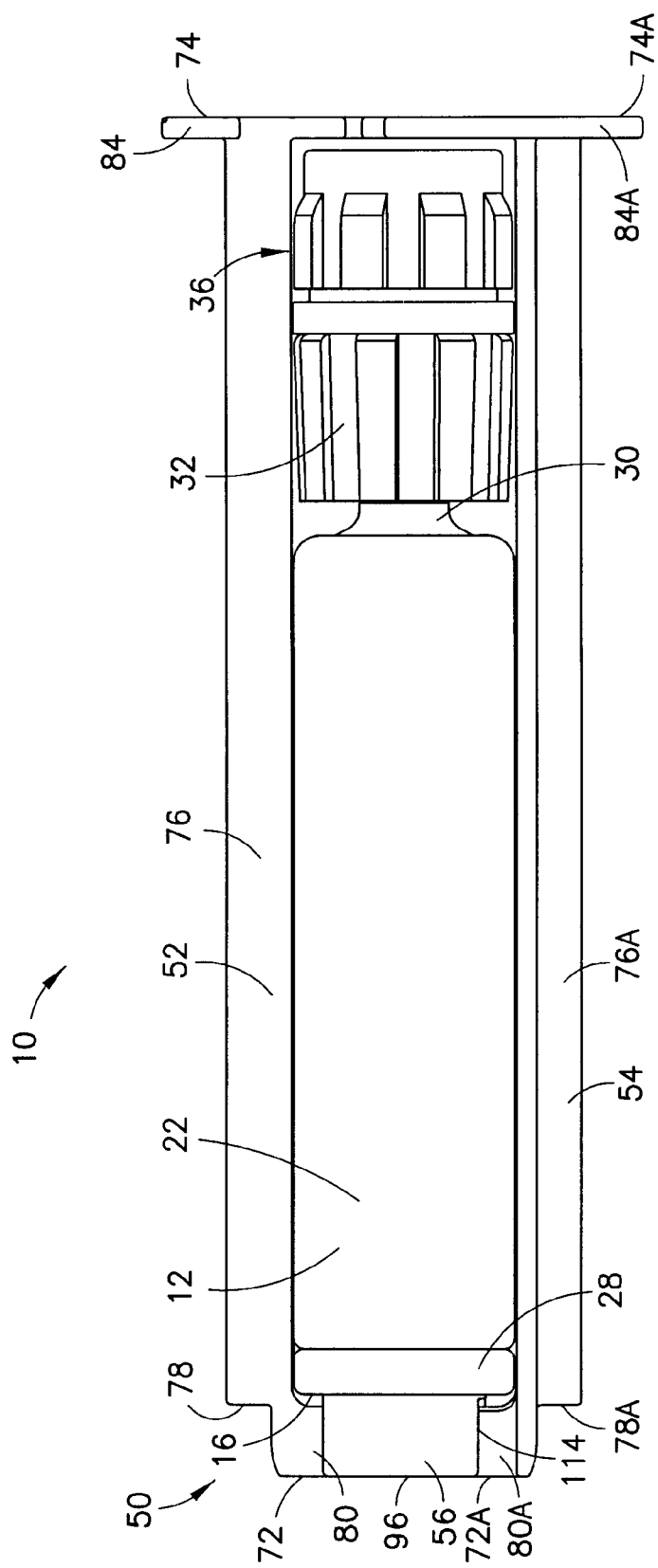
FIG. 4 is a rear view of the syringe assembly of FIG. 1 in accordance with an embodiment of the present invention.
Figure 5:
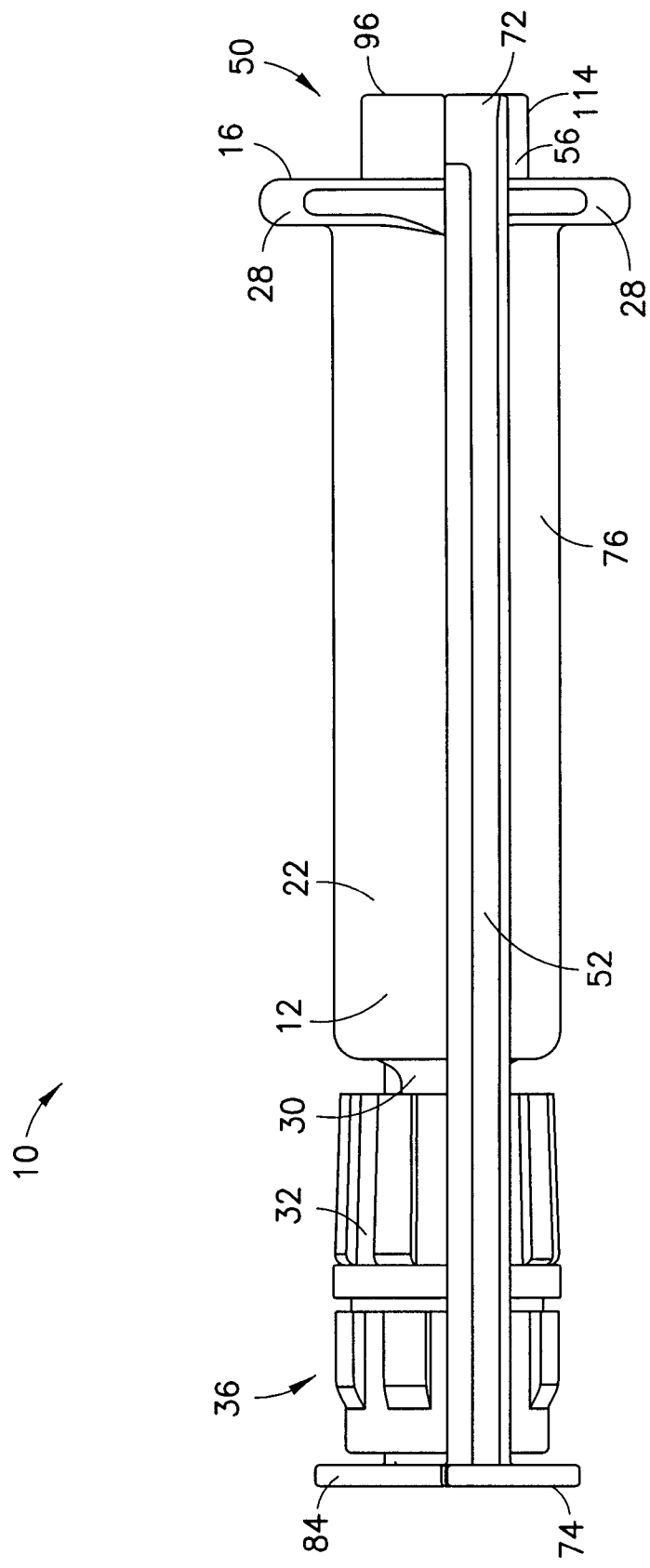
FIG. 5 is a top view of the syringe assembly of FIG. 1 in accordance with an embodiment of the present invention.
Figure 6:
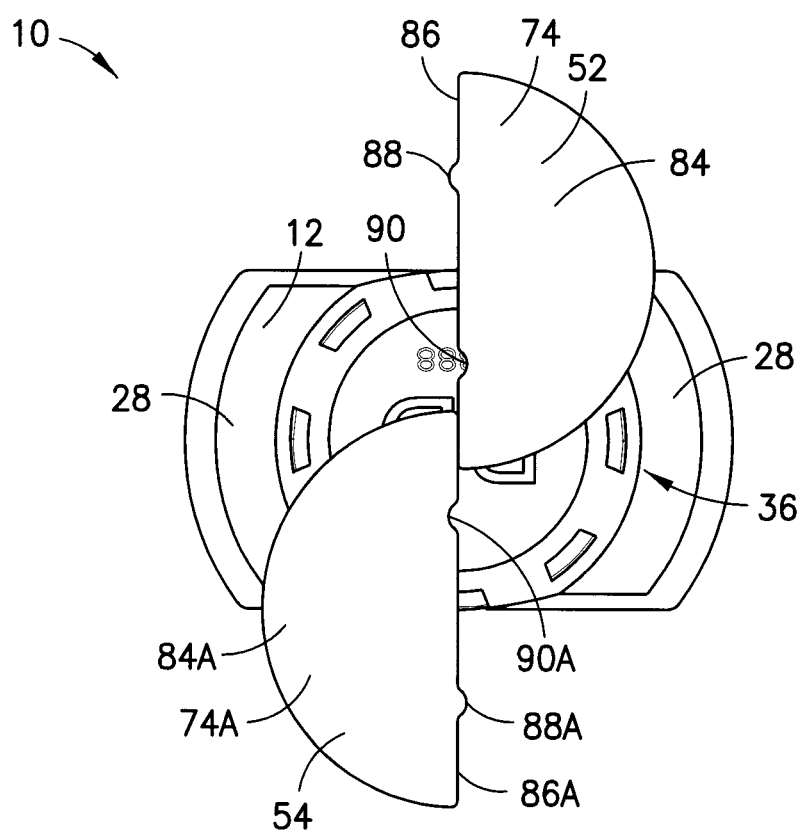
FIG. 6 is a left side view of the syringe assembly of FIG. 1 in accordance with an embodiment of the present invention.
Figure 7:
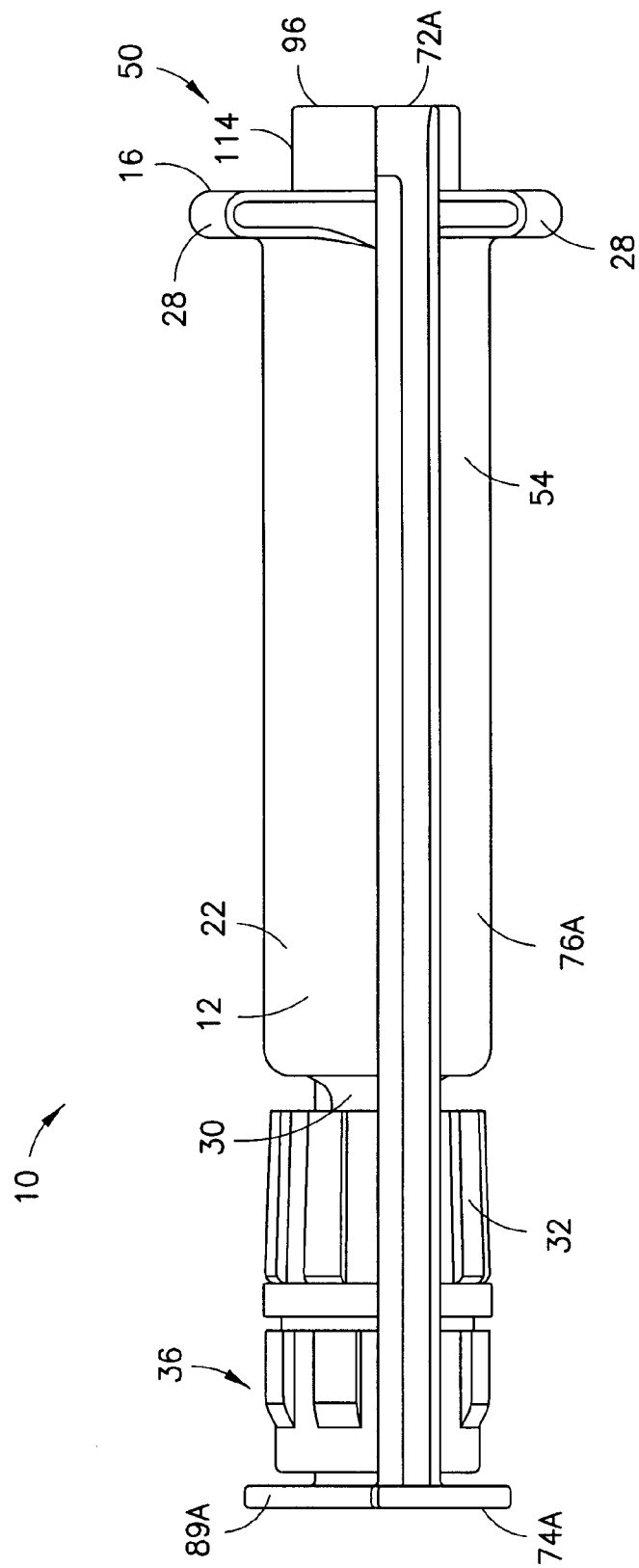
FIG. 7 is a bottom view of the syringe assembly of FIG. 1 in accordance with an embodiment of the present invention.
Figure 8:
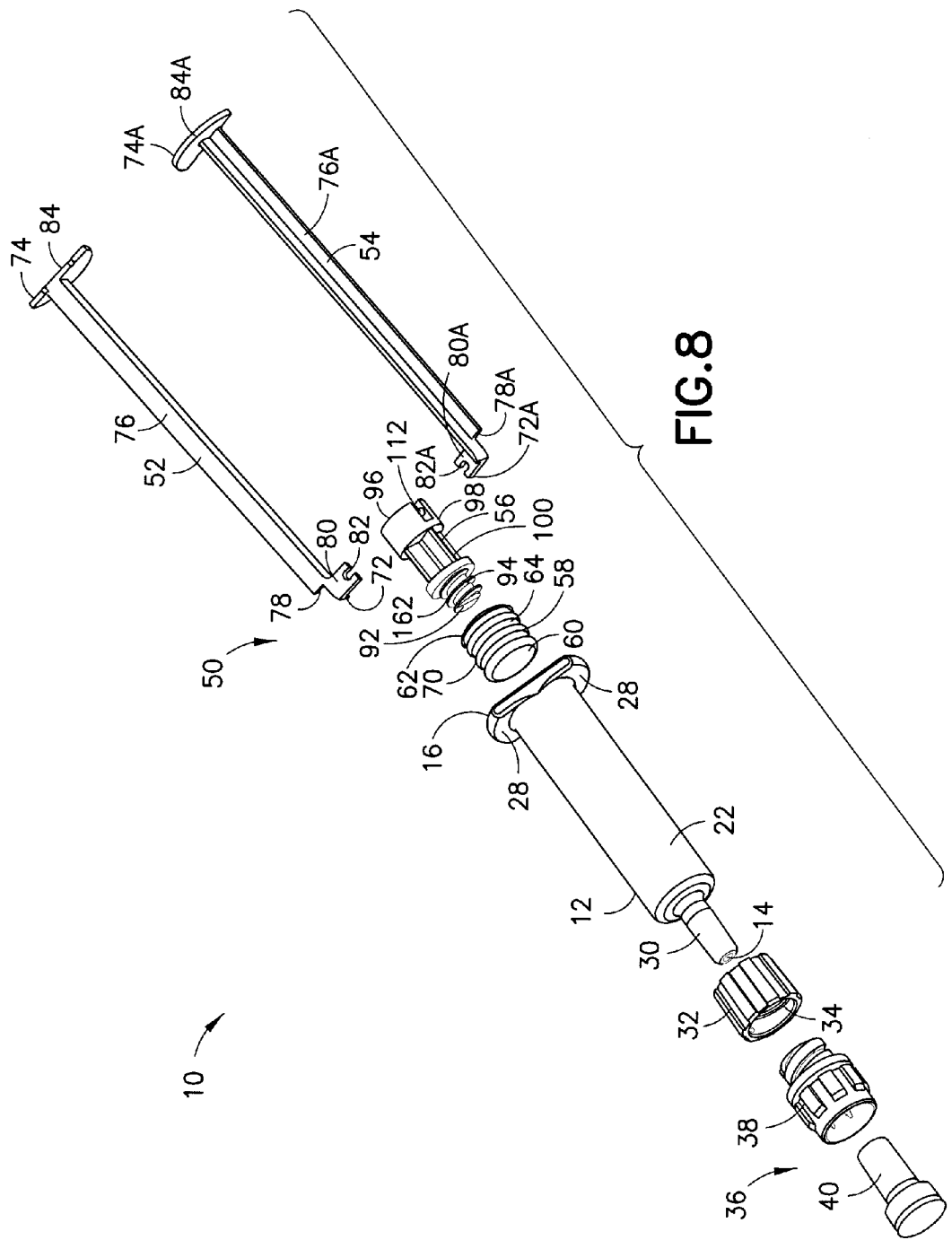
FIG. 8 is an exploded perspective view of the syringe assembly of FIG. 1 in accordance with an embodiment of the present invention.
Figure 9:
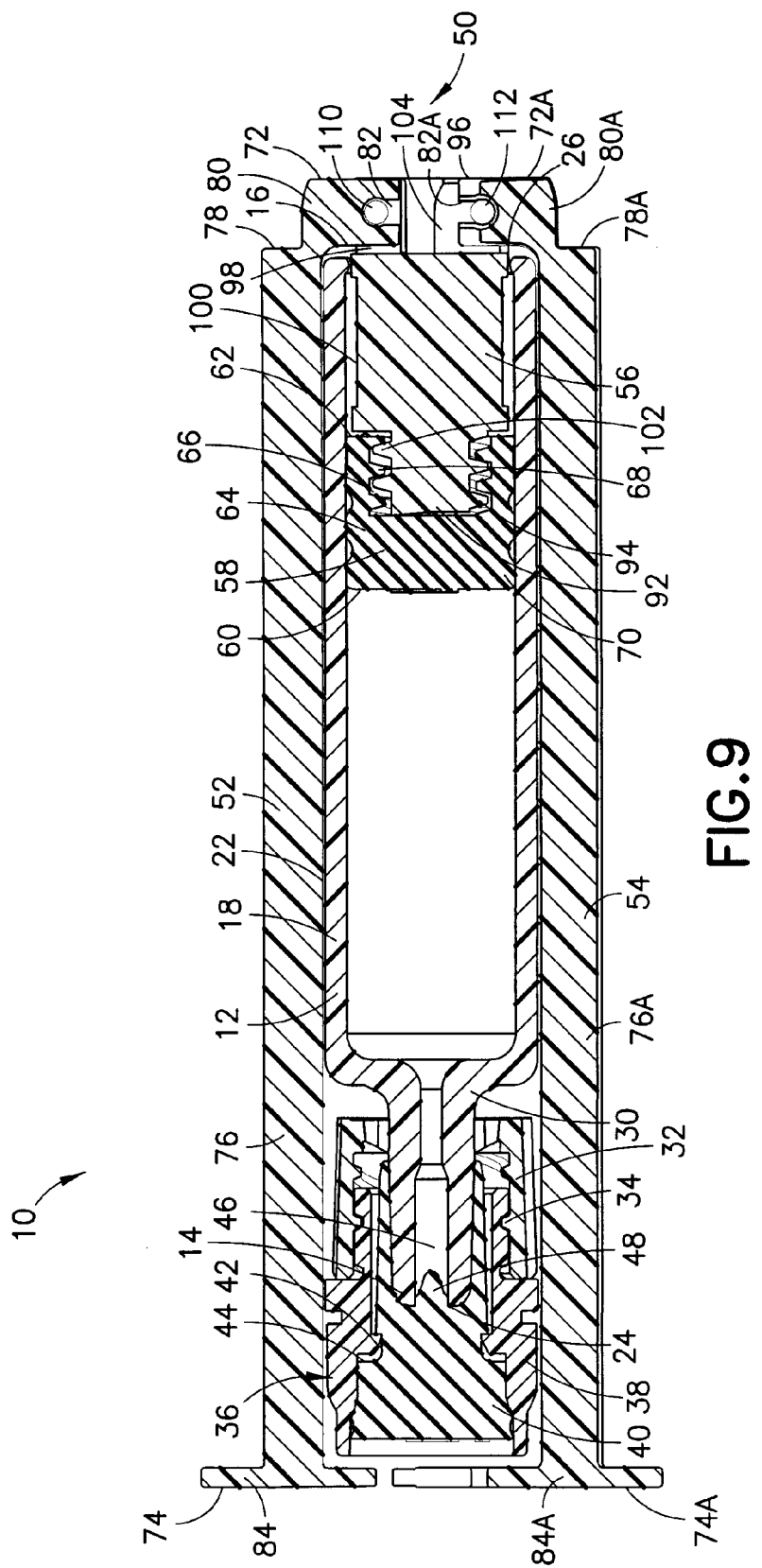
FIG. 9 is cross-sectional view of the syringe assembly of FIG. 1 in accordance with an embodiment of the present invention.
Figure 10:
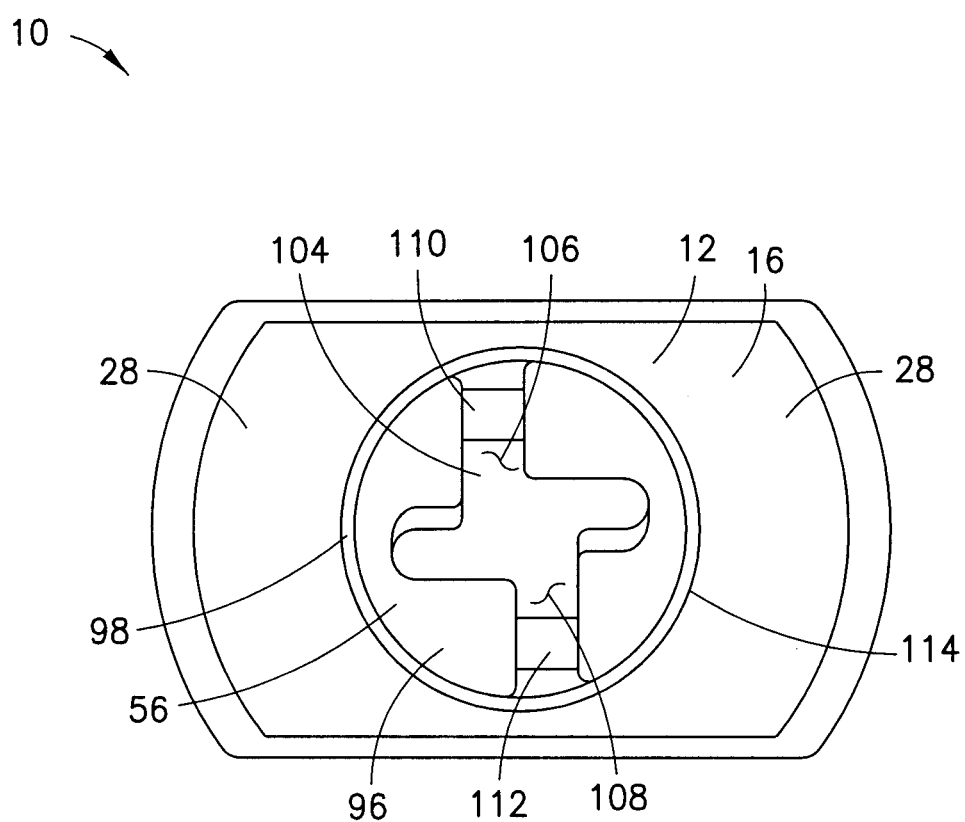
FIG. 10 is an enlarged right side view of the syringe assembly of FIG. 1 with the plunger arms removed in accordance with an embodiment of the present invention.
Figure 11:
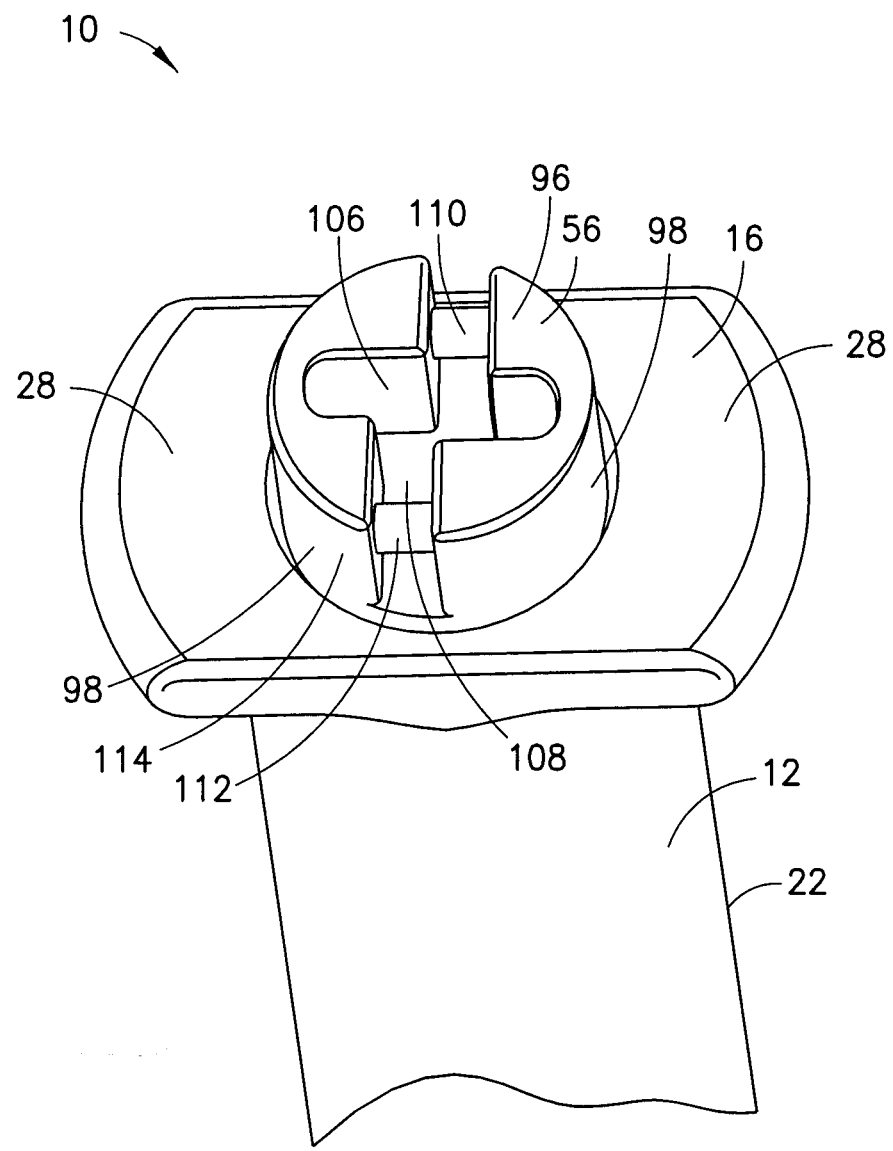
FIG. 11 is a partial perspective view of the syringe assembly of FIG. 1 with the plunger arms removed in accordance with an embodiment of the present invention.
Figure 12:
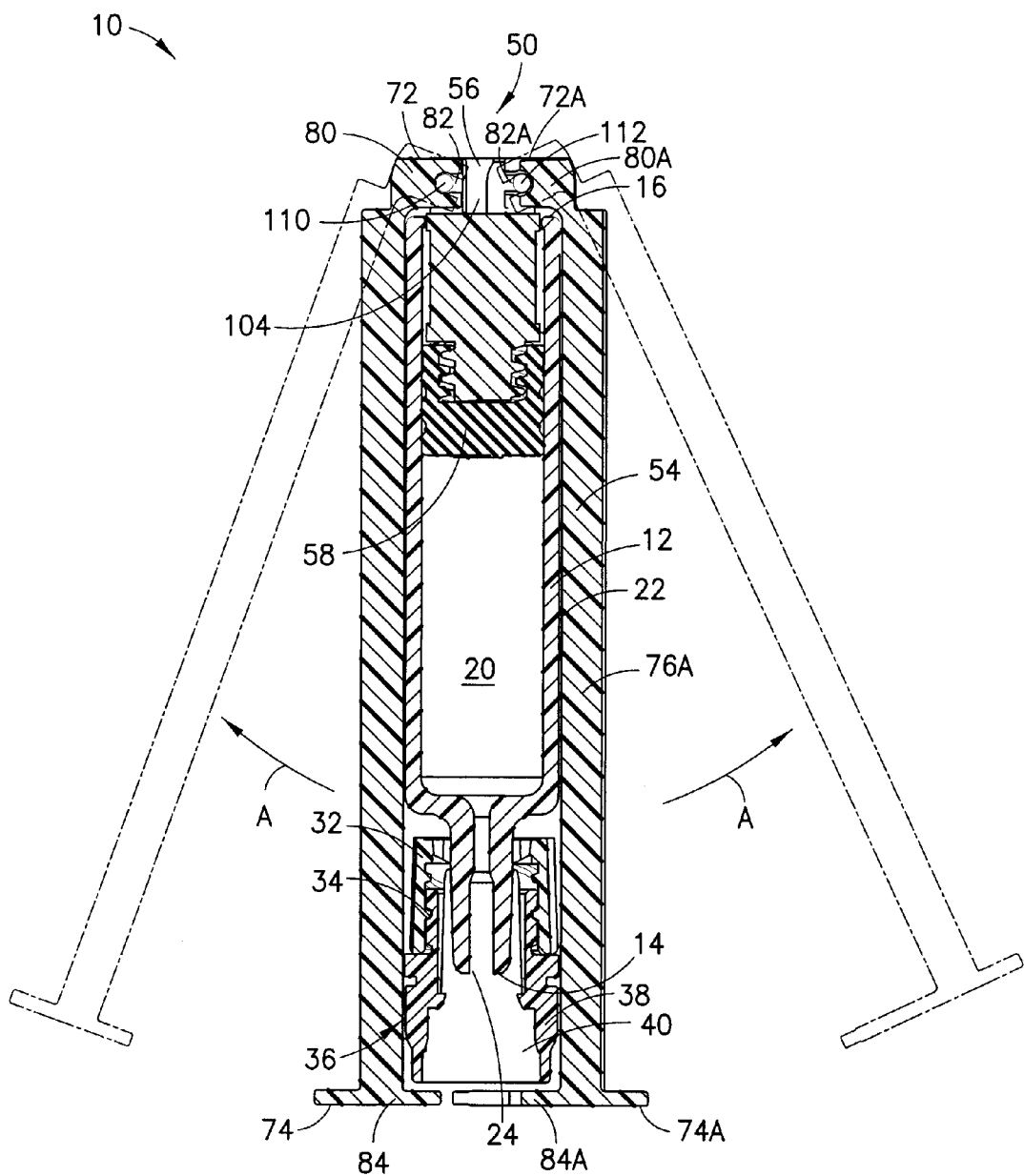
FIG. 12 is a cross-sectional view of the syringe assembly of FIG. 1 showing the plunger arms pivoting away from the syringe barrel in accordance with an embodiment of the present invention.

The syringe assembly 10 includes a syringe barrel 12 having a first or distal end 14 and a second or proximal end 16, with a sidewall 18 extending therebetween and defining an interior chamber 20 of the syringe barrel 12, as shown in FIG. 12. The syringe barrel 12 defines a longitudinal axis L, as shown in FIG. 2, extending in a longitudinal direction through the interior chamber 20 of the syringe barrel 12. The syringe barrel 12 has an external surface 22 and may be in the general form of an elongated cylindrical barrel, as is known in the art for the general shape of a hypodermic syringe, although other forms for containing a fluid for delivery are also contemplated by the present invention. The first end 14 of the syringe barrel 12 defines an outlet opening 24, and the second end 16 of the syringe barrel 12 defines a rearward opening 26. The syringe barrel 12 may be formed of glass, or may be injection molded from thermoplastic material such as polypropylene and polyethylene according to techniques known to those of ordinary skill in the art, though it is to be appreciated that the syringe barrel 12 may be made from other suitable materials and according to other applicable techniques. In certain configurations, the syringe barrel 12 may include outwardly extending flanges 28 about at least a portion of the second end 16. The flanges 28 may be configured for easy grasping by a medical practitioner, as will be discussed herein.

The syringe barrel 12 may include markings, such as graduations on the sidewall 18 thereof, for providing an indication as to the level or amount of fluid contained within the syringe barrel 12. Such markings may be provided on the external surface 22, the internal wall, or integrally formed or otherwise within the wall of syringe barrel. Alternatively, or in addition thereto, the markings may provide a description of the contents of the syringe, or other identifying information, as may be known in the art.

The first end 14 of syringe barrel 12 including the outlet opening 24 may have a profile adapted for engagement with a separate dispensing device, such as a needle assembly or IV connection assembly, and therefore may include a mechanism for such engagement, for example, a generally tapered luer tip 30, for engagement with a separate luer lock 32. In one configuration, both the tapered luer tip 30 and the separate luer lock 32 may be provided with the syringe assembly. In this configuration, the luer lock 32 may be provided with an attachment mechanism, such as a threaded engagement 34, for corresponding engagement with a cap assembly 36 having a cap body 38 and a seal 40. The seal 40 is secured within the cap body 38 and is configured to close and seal the outlet opening 24 of the first end 14 of the syringe barrel 12 when the cap assembly 36 is engaged with the luer lock 32. The seal 40 is secured within the cap body 38 via an inwardly extending protrusion 42 of the cap body 38 engaging a corresponding recessed portion 44 of the seal 40. The seal 40 defines an opening 46 that receives the luer tip 30 and includes a projection 48 positioned within the opening 46 that is configured to seal the outlet opening 24. In another configuration, the tapered luer tip 30 may be provided for direct engagement with a separate device (not shown). In addition, a mechanism for locking engagement therebetween may also be provided. Such luer connections and luer locking mechanisms are well known in the art.

The syringe assembly 10 further includes a plunger assembly 50, at least a portion of which is adapted to be disposed at least partially within the syringe barrel. The plunger assembly 50 provides a mechanism for dispensing fluid contained within the interior chamber 20 of the syringe barrel 12. In particular, the plunger assembly 50 includes first and second plunger arms 52, 54, a plunger adapter 56, and a stopper 58.

Referring again to FIGS. 1-11, the stopper 58 is positioned within the interior chamber 20 of the syringe barrel 12 at a position adjacent to the rearward opening 26 of the syringe barrel 12. The plunger adapter 56 may be secured to the stopper 58 via an engagement of a stopper engaging portion 94 with a threaded portion 68 in an opening 66 of the stopper 58, as discussed in more detail below. In one embodiment, the plunger adapter 56 is formed separately from the stopper 58. In another embodiment, the plunger adapter 56 may be formed integrally with the stopper 58.

The stopper 58 has a first end 60 and a second end 62 and includes an elongate body 64 that is generally cylindrical. In one embodiment, the elongate body 64 of the stopper 58 may define the opening 66 configured to receive the stopper engaging portion 94 of the plunger adapter 56. The stopper 58 may include the threaded portion 68 positioned within the opening 66 that is configured to receive and engage a threaded portion 102 of the stopper engaging portion 94 of the plunger adapter 56. The elongate body 64 of the stopper 58 also includes one or more annular ribs 70 extending about the outside of the stopper 58 for providing sealing engagement with the interior surface of the sidewall 18 of the syringe barrel 12.

The first and second plunger arms 52, 54 each have a first end 72, 72A and a second end 74, 74A. The plunger arms 52, 54 each have an elongate body 76, 76A that may be generally L-shaped in cross-section. The elongate body 76, 76A of each plunger arm 52, 54 defines a notched portion 78, 78A adjacent to the first end 72, 72A. The first end 72, 72A of each plunger arm 52, 54 includes an extension 80, 80A extending from the elongate body 76, 76A of each plunger arm 52, 54. Each extension 80, 80A extends from the respective elongate body 76, 76A substantially perpendicular to, such as at about a 90 degree angle, the elongate body 76, 76A. The extension 80, 80A of each plunger arm 52, 54 includes a receiver 82, 82A that is configured to receive respective engagements 110, 112 positioned on the plunger adapter 56. Each receiver 82, 82A is a slot-shaped opening defined by the extension 80, 80A of each plunger arm 52, 54, although other suitable arrangements for receiving an engagement may be utilized. The second end 74, 74A of each plunger arm 52, 54 includes a head portion 84, 84A extending from the elongate body 76, 76A of each plunger arm 52, 54. The head portion 84, 84A of each plunger arm 52, 54 is semi-spherical in shape and has a generally planar edge 86, 86A. The planar edge 86, 86A of the head portion 84, 84A of each plunger arm 52, 54 includes a locking protrusion 88, 88A and a locking recess 90, 90A spaced from the locking protrusion 88, 88A. The locking protrusion 88 and locking recess 90 of the first plunger arm 52 are configured to correspondingly engage the locking protrusion 88A and locking recess 90A of the second plunger arm 54. The first and second plunger arms 52, 54 are configured to abut each other such that the respective elongate bodies 76, 76A and respective planar edges 86, 86A are joined to each other to form a plunger rod configured to displace the stopper 58 relative to the syringe barrel 12. When the first and second plunger arms 52, 54 abut each other, the respective locking protrusions 88, 88A and locking recesses 90, 90A engage each other to secure the first plunger arm 52 to the second plunger arm 54. Further, the head portions 84, 84A of the first and second plunger arms 52, 54 are configured to form a thumb press when the respective planar edges 86, 86A are joined.

The plunger adapter 56 has a first end 92 with a stopper engaging portion 94, a second end 96 with a plunger interface portion 98, and an intermediate portion 100 positioned between the first and second ends 92, 96. The stopper engaging portion 94 of the plunger adapter 56 includes the threaded portion 102 configured to engage the corresponding threaded portion 68 of the stopper 58. The threaded portion 102 is a helical thread, although other suitable arrangements may be utilized. The plunger interface portion 98 of the plunger adapter 56 defines a recessed portion 104. As shown more clearly in FIGS. 10 and 11, the recessed portion 104 includes a first L-shaped area 106 configured to receive a portion of the extension 80 of the first plunger arm 52 and a portion of the elongate body 76 of the first plunger arm 52, and a second L-shaped area 108 configured to receive a portion of the extension 80A of the second plunger arm 54 and a portion of the elongate body 76A of the second plunger arm 54. The first L-shaped area 106 and the second L-shaped area 108 are offset relative to each other in a direction perpendicular to the longitudinal axis L of the syringe barrel. The plunger interface portion 98 of the plunger adapter 56 includes the first engagement 110 positioned within the first L-shaped area 106 and configured to be received by the receiver 82 of the first plunger arm 52 and to allow pivotal movement of the first plunger arm 52 relative to the plunger adapter 56. The plunger interface portion 98 of the plunger adapter 56 also includes the second engagement 112 positioned within the second L-shaped area 108 and configured to be received by the receiver 82A of the second plunger arm 54 and to allow pivotal movement of the second plunger arm 54 relative to the plunger adapter 56. The first and second engagements 110, 112 each may be a pin-shaped member generally having a cylindrical shape, although other suitable arrangements for the engagements may be utilized. The first and second engagements 110, 112 of the plunger adapter 56 are spaced radially inward from an external surface 114 of the plunger adapter 56 and are offset relative to each other in a direction perpendicular to the longitudinal axis L of the syringe barrel 12. The intermediate portion 100 of the plunger adapter 56 is generally cross-shaped in cross-section, although other suitably shaped portions may be provided between the plunger interface portion and the stopper engaging portion.

The first end 72, 72A of each plunger arm 52, 54 is pivotally secured to the plunger adapter 56 via the connection of the respective receivers 82, 82A of the plunger arms 52, 54 with the respective first and second engagements 110, 112 of the plunger adapter 56. In particular, the first and second engagements 110, 112 of the plunger adapter 56 each have a friction fit with the respective receivers 82, 82A of the first and second plunger arms 52, 54 to separately secure the plunger arms 52, 54 to the plunger adapter 56 and stopper 58 while still allowing pivotal movement of the first and second plunger arms 52, 54 relative to the plunger adapter 56. Although a friction fit arrangement is disclosed, other suitable arrangements for pivotally securing the plunger arms to the plunger adapter may be utilized.

As discussed in more detail below, the first and second plunger arms 52, 54 each have a pre-use position (shown in FIG. 12) and a use position (shown in FIG. 13). In the pre-use position, the second end 74, 74A of each plunger arm 52, 54 is positioned adjacent to the cap assembly 36. The first and second plunger arms 52, 54 are each substantially parallel to the longitudinal axis L of the syringe barrel 12, and the plunger interface portion 98 of the plunger adapter 56 is positioned outside of the chamber 20 of the syringe barrel 12 when the first and second plunger arms 52, 54 are in the pre-use position. In the use position, the second end 74, 74A of each plunger arm 52, 54 is spaced from the syringe barrel 12 along the longitudinal axis L and the first plunger arm 52 is positioned adjacent to the second plunger arm 54 to form a plunger rod that is configured to displace the stopper 58 relative to the syringe barrel 12. In particular, in the use position, the respective elongate bodies 76, 76A and respective planar edges 86, 86A are joined to each other and the respective locking protrusions 88, 88A and locking recesses 90, 90A engage each other to secure the first plunger arm 52 to the second plunger arm 54. Further, the head portions 84, 84A of the first and second plunger arms 52, 54 form a thumb press when the respective planar edges 86, 86A are joined and the first and second plunger arms 52, 54 are in the use position. The first and second plunger arms 52, 54 are substantially aligned with the longitudinal axis L of the syringe barrel 12 when the plunger arms 52, 54 are in the use position. When the plunger arms 52, 54 are in the pre-use position and the use-position, the recessed portion 104 of the plunger adapter 56 receives at least a portion of the first ends 72, 72A of each of the first and second plunger arms 52, 54. In particular, the first L-shaped area 106 of the recessed portion 104 of the plunger adapter 56 receives a portion of the extension 80 of the first plunger arm 52, and the second L-shaped area 108 of the recessed portion 104 of the plunger adapter 56 receives a portion of the extension 80A of the second plunger arm 54. In the use position, the first and second L-shaped areas 106, 108 further receive a portion of the respective elongate bodies 76, 76A of the first and second plunger arms 52, 54.

The syringe assembly 10 is particularly useful as a pre-filled syringe, and therefore may be provided for end use with a fluid, such as a medication, contained within interior chamber 20 of syringe barrel 12, pre-filled by the manufacturer. In this manner, the syringe assembly 10 can be manufactured, pre-filled with a medication, sterilized, and optionally packaged in separate packaging, for delivery, storage, and use by the end user, without the need for the end user to fill the syringe with medication from a separate vial prior to use.

Figure 13:
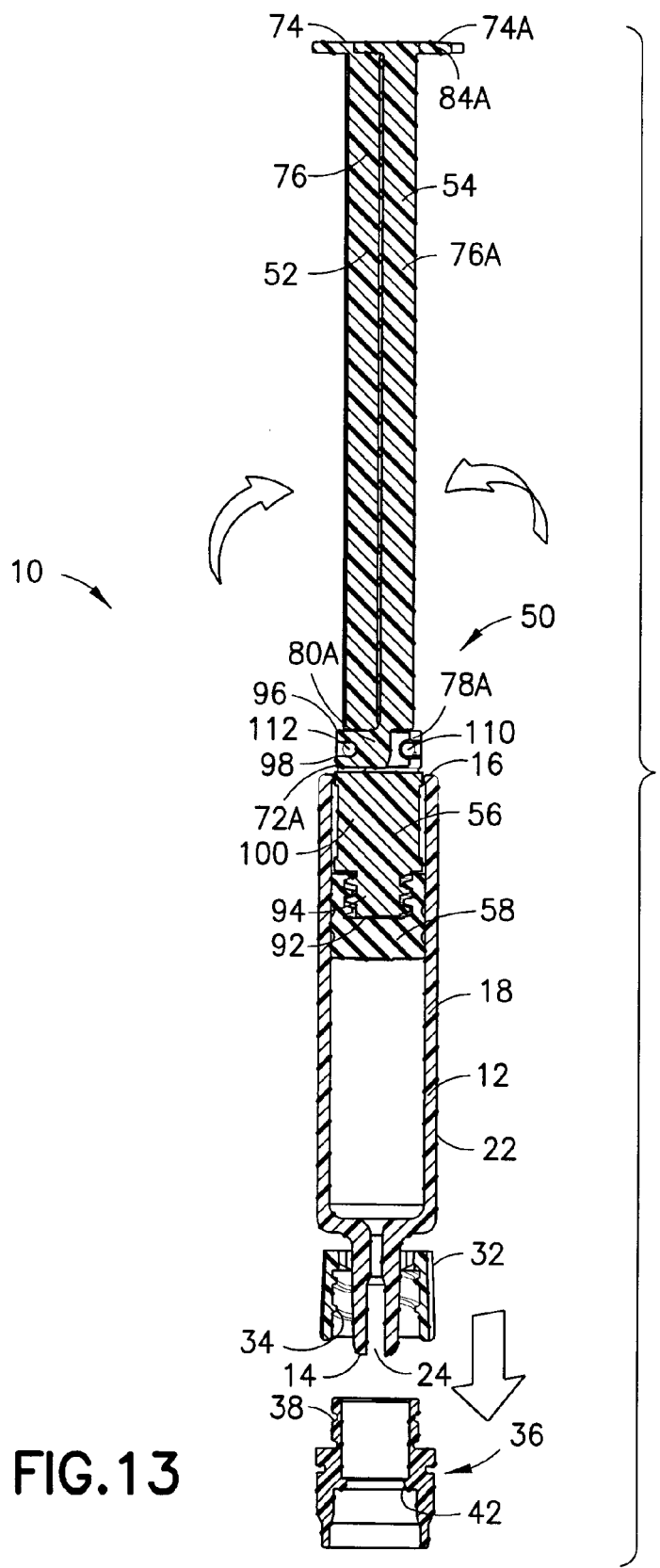
FIG. 13 is a cross-sectional view of the syringe assembly of FIG. 1 showing the plunger arms in a use position in accordance with an embodiment of the present invention.
Figure 14:
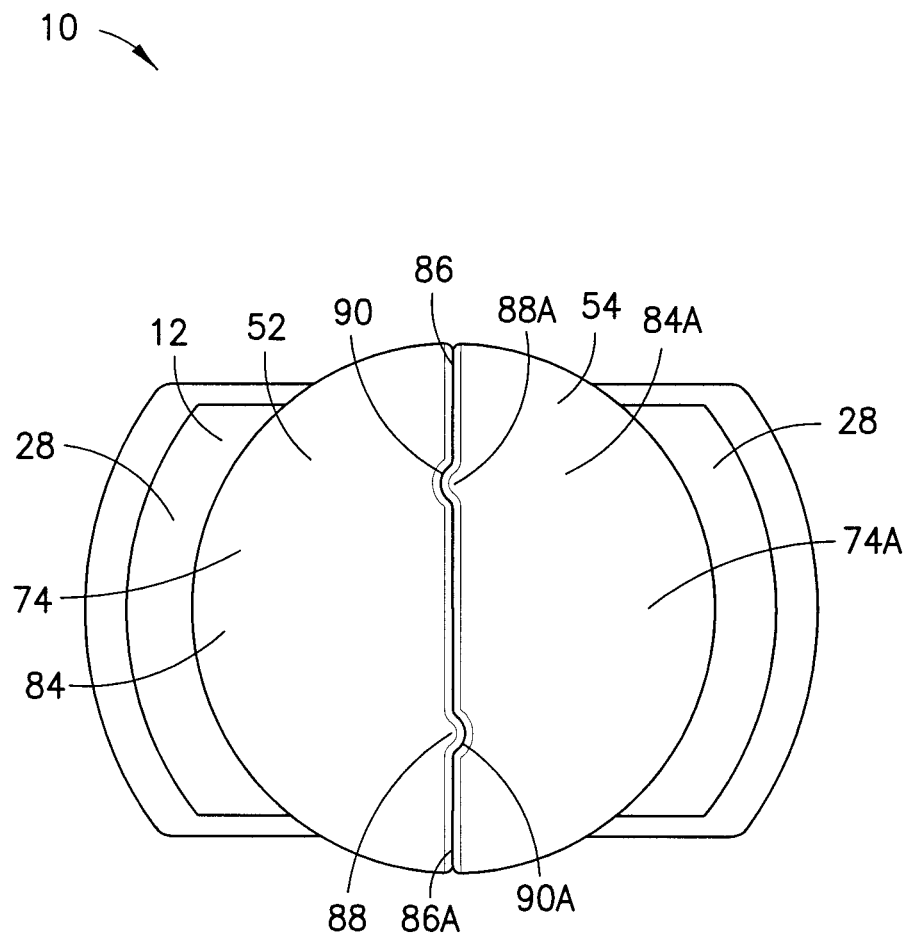
FIG. 14 is a right side view of the syringe assembly of FIG. 1 showing the plunger arms in a use position in accordance with an embodiment of the present invention.

Referring to FIGS. 12-16B, in use, a user manually pivots each of the plunger arms 52, 54 from the pre-use position (shown in FIG. 12) to the use position (shown in FIG. 13). As shown in FIG. 12, the second end 74, 74A of each plunger arm 52, 54 is pivoted away from the syringe barrel 12 in a first direction A. The position of each plunger arm 52, 54 between the pre-use position and the use position is shown in phantom lines in FIG. 12. As shown in FIG. 13, the cap assembly 36 is removed from the first end 14 of the syringe barrel and the second end 74, 74A of each plunger arm 52, 54 is further pivoted in the first direction A (shown in FIG. 12) until each plunger arm 52, 54 is in the use position with continued pivoting of each plunger arm 52, 54 being restricted by engagement of the first end 72, 72A of each plunger arm 52, 54 with the plunger adapter 56. In particular, as shown more clearly in FIGS. 13, 16A, and 16B, the recessed portion 104 of the plunger adapter 56 receives the extension 80, 80A of each plunger arm 52, 54 and a portion of the respective elongate bodies 76, 76A of the plunger arms 52, 54 thereby preventing continued pivoting in the first direction A. In other words, the recessed portion 104 of the plunger adapter 56 receives the first end 72, 72A of each plunger arm 52, 54 and acts as a stop to prevent further pivoting of the first and second plunger arms 52, 54 in the first direction A when the first and second plunger arms 52, 54 reach the use position. Further, as shown in FIG. 14, in the use position, the respective locking protrusions 88, 88A and locking recesses 90, 90A of the first and second plunger arms 52, 54 engage each other to secure the first plunger arm 52 to the second plunger arm 54.

Furthermore, the first and second plunger arms 52, 54 are stabilized in the use position through the positioning of the first end 72, 72A of each plunger arm 52, 54 within the recessed portion 104. More specifically, a portion of the respective elongate bodies 76, 76A of the first and second plunger arms 52, 54 is received by the first and second L-shaped areas 106, 108 of the recessed portion 104 and provides multiple engagement surfaces 116 to stabilize the first and second plunger arms 52, 54 when in the use position. The engagement surfaces 116 are offset from each other in a direction perpendicular to the longitudinal axis L of the syringe barrel 12 which stabilizes the plunger arms 52, 54 when torque is applied to the plunger arms 52, 54 during deployment thereof into the syringe barrel 12. Also, pivoting of the first and second plunger arms 52, 54 from the pre-use position to the use position is stabilized due to the positioning of the extension 80, 80A of each plunger arm 52, 54 within the respective L-shaped areas 106, 108 of the recessed portion 104 of the plunger adapter 56 during movement from the pre-use position to the use position. In particular, positioning the respective extensions 80, 80A of the plunger arms 52, 54 within the respective L-shaped areas 106, 108 of the recessed portion 104 in the pre-use position provides engagement surfaces 118 on each side of the respective extensions 80, 80A to stabilize the pivoting movement of the first and second plunger arms 52, 54.

Figure 15:
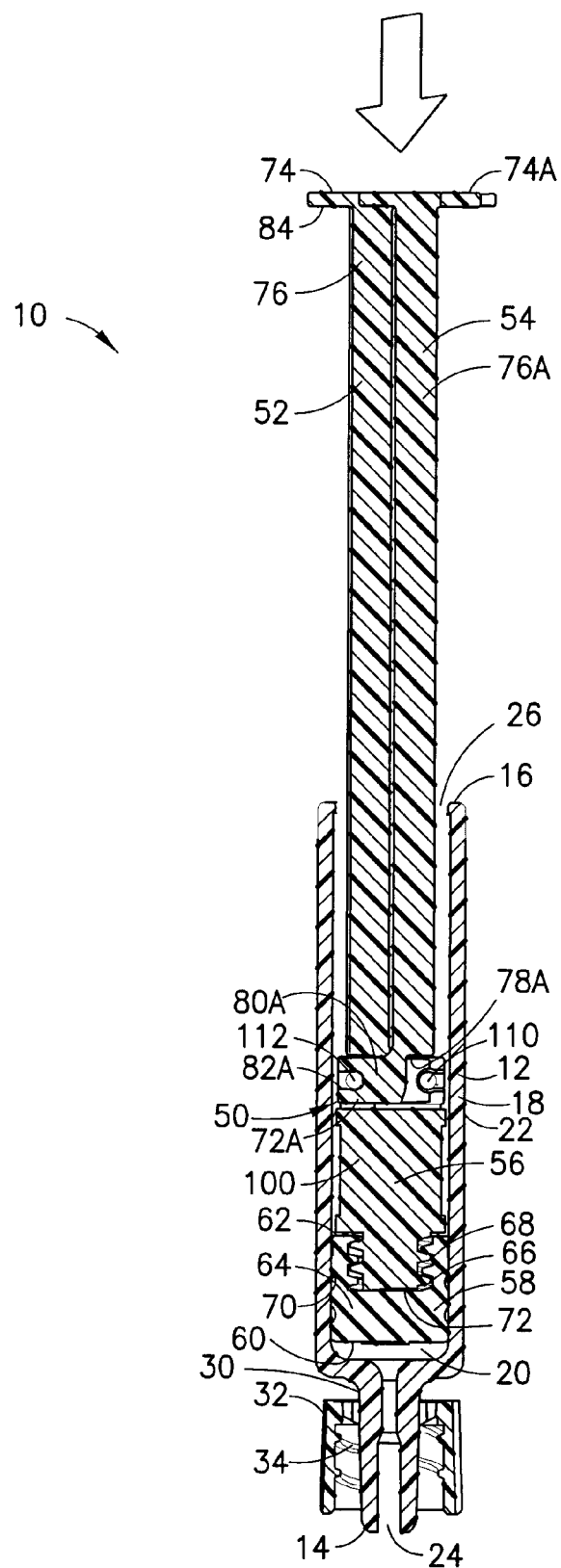
FIG. 15 is a cross-sectional view of the syringe assembly of FIG. 1 showing the plunger arms in a depressed position in accordance with an embodiment of the present invention.
Figure 16A:
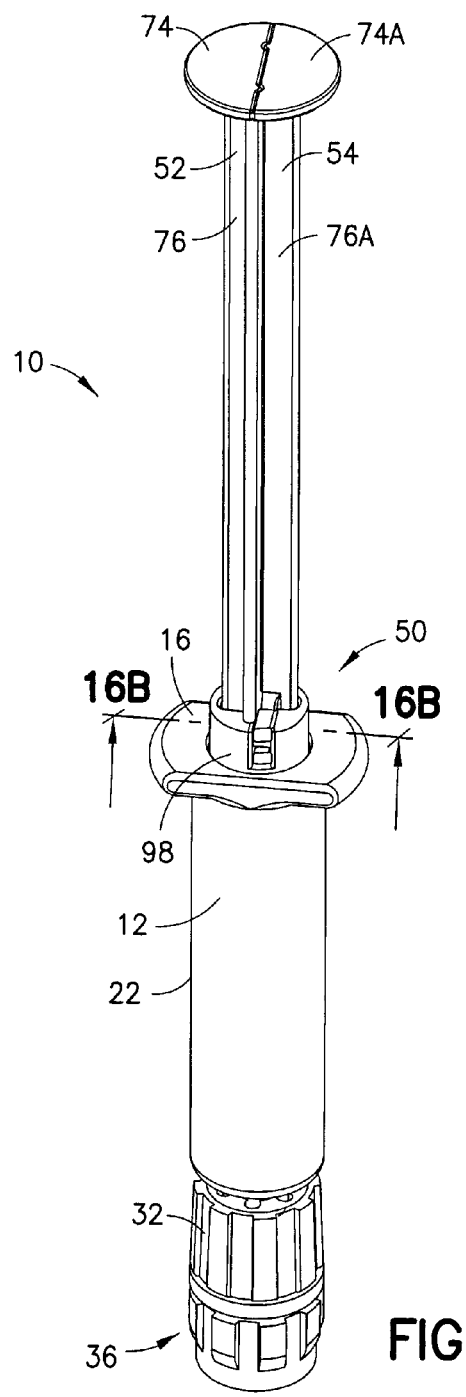
FIG. 16A is a front perspective view of the syringe assembly of FIG. 1 in accordance with an embodiment of the present invention.
Figure 16B:
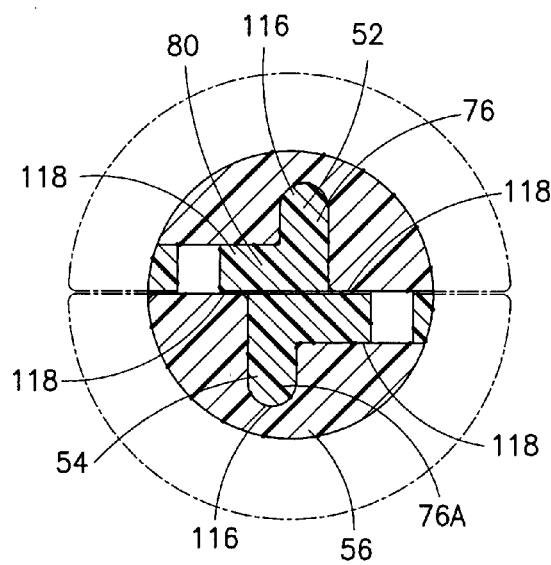
FIG. 16B is a cross-sectional view taken along line 16B-16B of FIG. 16A showing the plunger rod in a use position in accordance with an embodiment of the present invention.

When the first and second plunger arms 52, 54 are in the use position, the syringe assembly 10 can be grasped with the user's thumb on the respective head portions 84, 84A forming the thumb press and with the user's fingers grasping the flanges 28. In this manner, the syringe assembly 10 is grasped by the user in a well known and well recognized manner. As shown in FIG. 15, the user effects a squeezing movement between the thumb and forefingers thereby depressing the plunger arms 52, 54 into the rearward opening 26 of the syringe barrel 12. Such movement transfers to the plunger adapter 56 and stopper 58 causing movement of the stopper 58 and plunger adapter 56 within the interior chamber 20 of the syringe barrel 12, reducing the volume of the interior chamber 20, and creating a positive pressure therein.

Prior to the dispensing of medication, any air trapped within interior chamber 20 may be expelled by initial movement of the plunger arms 52, 54 into syringe barrel 12 in a known manner. The user can attach luer tip 30 to a separate needle assembly or IV connection assembly and lockingly engage through threads 34 of the luer lock 32 in a known manner. The medication fluid within interior chamber 20 is forced out through outlet opening 24 at first end 14 of syringe barrel 12. In this manner, the fluid medication can be expelled from the syringe barrel 12 through outlet opening 24 and into the separate needle assembly or IV assembly and into the patient.

Upon full movement of the stopper 58 through syringe barrel 12, the stopper 58 "bottoms out". The stopper 58, as shown in FIG. 15, is not fully depressed and is just short of bottoming out. After bottoming out and dispensing all of the fluid within the interior chamber 20 of the syringe barrel 12, the syringe assembly 10 can be detached from the patient and appropriately discarded. Although the use of the syringe assembly 10 was described in connection with a pre-filled syringe, the syringe assembly 10 may also be utilized for aspiration by moving the stopper 58 to the position shown in FIG. 15 and retracting the stopper 58 by moving the second ends 74, 74A of the first and second plunger arms 52, 54 away from the syringe barrel 12.

The syringe assembly 10 may be positioned within a separate container or package prior to use. In particular, the syringe assembly 10 may be packaged within a blister pack, as is known in the art, although other suitable package arrangements may be utilized. Further, in storage, the syringe assembly 10 may be placed in a controlled environment in which space is limited. The profile of the syringe assembly 10 of the present invention, however, is significantly reduced from conventional pre-filled syringes having the plunger extending from the barrel prior to use. In particular, pivotally securing the first and second plunger arms 52, 54 to the plunger adapter 56 and stopper 58 reduces the length of the syringe assembly 10 from conventional pre-filled syringes.

While several embodiments of a syringe assembly were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A syringe assembly comprising:
    a syringe barrel having a first end, a second end, and a sidewall extending between the first end and the second end, the sidewall defining a chamber;
    a stopper disposed within the chamber of the syringe barrel;
    a plunger adapter engaged with the stopper, the plunger adapter defining a recessed portion therein; and
    first and second plunger arms each having a first end pivotally secured to the plunger adapter and a second end, the first and second plunger arms each having a pre-use position wherein the first and second plunger arms are spaced from each other, and a use position wherein the first and second plunger arms abut each other and are configured to displace the stopper relative to the syringe barrel, the recessed portion of the plunger adapter receiving a portion of a first end of a plunger rod when the first and second plunger arms are in the pre-use position and the use position,
    wherein, in the use position, the first ends of the first and second plunger arms are received by the recessed portion providing multiple engagement surfaces thereby stabilizing the first and second plunger arms.

2. The syringe assembly of claim 1, wherein the stopper and the plunger adapter are co-formed.

3. The syringe assembly of claim 1, wherein the first and second plunger arms each comprise an elongate body, the first end of each plunger arm including one of a receiver and an engagement pivotally secured to another of a receiver and an engagement positioned on the plunger adapter.

4. A syringe assembly comprising:
    a syringe barrel having a first end, a second end, and a sidewall extending between the first end and the second end, the sidewall defining a chamber;
    a stopper disposed within the chamber of the syringe barrel;
    a plunger adapter engaged with the stopper, the plunger adapter defining a recessed portion therein; and
    first and second plunger arms each comprising an elongate body having a first end and a second end, the first end of each plunger arm including one of a receiver and an engagement and another of a receiver and an engagement engaged with the plunger adapter, wherein the receiver is pivotally secured with the engagement, the first and second plunger arms each having a pre-use position wherein the first and second plunger arms are spaced from each other, and a use position wherein the first and second plunger arms abut each other and are configured to displace the stopper relative to the syringe barrel,
    wherein, in the use position, the first ends of the first and second plunger arms are received by the recessed portion providing multiple engagement surfaces thereby stabilizing the first and second plunger arms.

5. The syringe assembly of claim 4, wherein the stopper and the plunger adapter are co-formed.

6. The syringe assembly of claim 4, wherein the first and second plunger arms are secured to each other when the first and second plunger arms are in the use position.

7. The syringe assembly of claim 4, wherein the first and second plunger arms are substantially parallel to a longitudinal axis of the syringe barrel when the first and second plunger arms are in the pre-use position.

8. The syringe assembly of claim 7, wherein the first plunger arm is positioned on an opposite side of the syringe barrel relative to the second plunger arm when the first and second plunger arms are in the pre-use position.

9. The syringe assembly of claim 6, wherein the first plunger arm has a locking protrusion and the second plunger arm has a locking recess configured to receive and engage the locking protrusion of the first plunger arm.

10. The syringe assembly of claim 4, wherein at least a portion of the elongate body of each plunger arm is substantially L-shaped in cross-section.

11. The syringe assembly of claim 4, wherein the plunger adapter is formed separately from the stopper and comprises a stopper engaging portion secured to the stopper and a plunger interface portion secured to the first and second plunger arms.

12. The syringe assembly of claim 11, wherein the plunger interface portion of the plunger adapter is positioned outside of the chamber when the first and second plunger arms are in the pre-use position.

13. The syringe assembly of claim 4, wherein the first end of each plunger arm includes an extension extending from the elongate body of each plunger arm, and wherein the receiver is positioned on the extension of the first end of each plunger arm and the engagement is positioned on the plunger adapter.

14. The syringe assembly of claim 13, wherein each receiver comprises an opening corresponding to the extension of the first end of each plunger arm, and wherein the engagement comprises a pin-shaped member configured to be received by the respective receivers of the first and second plunger arms.

15. The syringe assembly of claim 14, wherein the plunger adapter includes a first engagement configured to engage the receiver of the first plunger arm and a second engagement configured to engage the receiver of the second plunger arm.

16. The syringe assembly of claim 4, further comprising a medication or drug disposed within the syringe barrel.

17. A syringe assembly comprising:
a syringe barrel having a first end, a second end, and a sidewall extending between the first end and the second end, the sidewall defining a chamber with a longitudinal axis extending therealong;
a stopper disposed at least partially within the chamber;
a plunger adapter engaged with the stopper, the plunger adapter defining a recessed portion; and
first and second plunger arms each having a first end pivotally secured to the plunger adapter and transitionable from a pre-use position in which a portion of the first end of each plunger arm is secured to the plunger adapter and the first and second plunger arms extend adjacent to the syringe barrel, to a use position in which the first end of each plunger arm is entirely received within the recessed portion and the first and second plunger arms abut each other,
wherein, in the use position, the first ends of the first and second plunger arms are received by the recessed portion providing multiple engagement surfaces thereby stabilizing the first and second plunger arms.

18. A syringe assembly comprising:
a syringe barrel having a first end, a second end, and a sidewall extending between the first end and the second end, the sidewall defining a chamber with a longitudinal axis extending therealong;
a stopper disposed at least partially within the chamber;
a plunger adapter engaged with the stopper, the plunger adapter defining a recessed portion; and
first and second plunger arms each having a first end pivotally secured to the plunger adapter and transitionable from a pre-use position in which a portion of the first end of each plunger arm is secured to the plunger adapter and the first and second plunger arms extend adjacent to the syringe barrel, to a use position in which the first end of each plunger arm is entirely received within the recessed portion and the first and second plunger arms are positioned adjacent to each other,
wherein, in the use position, the first ends of the first and second plunger arms are received by the recessed portion providing multiple engagement surfaces thereby stabilizing the first and second plunger arms, and
wherein the recessed portion comprises a first L-shaped area configured to receive a portion of the first plunger arm, and a second L-shaped area configured to receive a portion of the second plunger arm.

19. The syringe assembly of claim 18, wherein the first L-shaped area is offset from the second L-shaped area in a direction perpendicular to the longitudinal axis.

20. The syringe assembly of claim 17, wherein the first and second plunger arms each comprise an elongate body, the first end of each plunger arm including a receiver pivotally secured to respective first and second engagements positioned on the plunger adapter.

21. The syringe assembly of claim 20, wherein the first and second engagements of the plunger adapter are offset from each other in a direction perpendicular to the longitudinal axis.

22. The syringe assembly of claim 1, wherein the first and second plunger arms each comprise an elongate body and a planar edge and wherein the elongate bodies of the first and second plunger arms and their respective planar edges are joined to each other in the use position to form the plunger rod.

23. The syringe assembly of claim 6, wherein the first and second plunger arms, each comprise a locking protrusion and a locking recess and wherein the locking protrusion and the locking recess of the respective first and second plunger arms are configured to engage each other to secure the first and second plunger arms to each other when in the use position.

24. The syringe assembly of claim 10, wherein the L-shaped portions of the elongate body of each plunger arm are configured to engage each other in a complimentary manner when in the use position.

* * * * *